(12) United States Patent
Vera-Ciro et al.

(10) Patent No.: US 12,198,789 B2
(45) Date of Patent: *Jan. 14, 2025

(54) EFFICIENT CRAWLING USING PATH SCHEDULING, AND APPLICATIONS THEREOF

(71) Applicant: VEDA Data Solutions, Inc., Washington, DC (US)

(72) Inventors: Carlos Vera-Ciro, Madison, WI (US); Robert Raymond Lindner, Fitchburg, WI (US)

(73) Assignee: VEDA Data Solutions, Inc., Madison, WI (US)

( * ) Notice: Subject to any disclaimer, the term of this patent is extended or adjusted under 35 U.S.C. 154(b) by 317 days.

This patent is subject to a terminal disclaimer.

(21) Appl. No.: 16/668,524

(22) Filed: Oct. 30, 2019

(65) Prior Publication Data

US 2021/0134407 A1    May 6, 2021

(51) Int. Cl.
| | |
|---|---|
| *G16H 10/60* | (2018.01) |
| *G06F 16/21* | (2019.01) |
| *G06F 40/14* | (2020.01) |
| *G16H 40/20* | (2018.01) |
| *G16H 50/20* | (2018.01) |
| *G16H 50/70* | (2018.01) |

(52) U.S. Cl.
CPC .............. *G16H 10/60* (2018.01); *G06F 16/21* (2019.01); *G06F 40/14* (2020.01); *G16H 40/20* (2018.01); *G16H 50/20* (2018.01); *G16H 50/70* (2018.01)

(58) Field of Classification Search
CPC ........ G16H 10/60; G16H 40/20; G16H 50/70; G16H 50/20; G06F 16/21; G06F 40/14; G06F 16/951
USPC ......................................................... 707/797
See application file for complete search history.

(56) References Cited

U.S. PATENT DOCUMENTS

| | | | |
|---|---|---|---|
| 5,664,109 A * | 9/1997 | Johnson ................. | G16H 10/60 706/45 |
| 6,606,625 B1 * | 8/2003 | Muslea ................. | G06F 16/951 |
| 6,714,941 B1 * | 3/2004 | Lerman ................. | G06F 16/951 707/999.102 |

(Continued)

OTHER PUBLICATIONS

Hong-ye, C., "Method of Web Information Extraction Based on Decision Tree," 2009, IEEE, pp. 664-666.*

(Continued)

*Primary Examiner* — James T Tsai
(74) *Attorney, Agent, or Firm* — Sterne, Kessler, Goldstein, Fox, P.L.L.C.

(57) ABSTRACT

The present disclosure is directed to systems and methods for extracting unstructured data from a data source in a structure manner. Embodiments provide ways to retrieve unstructured data along from data sources not optimized for automated retrieval. For example, embodiments may generate a branched tree for each data source that maps out paths to individual sites of, for example, a healthcare provider listing the unstructured data. Using this branched tree, tasks can be generated to navigate along a path with the data source to each site and extract the unstructured data from the data source. In this way, embodiments provide the ability to navigate through a site from a base site to a site that has the relevant data.

20 Claims, 12 Drawing Sheets

(56) References Cited

U.S. PATENT DOCUMENTS

| | | | | |
|---|---|---|---|---|
| 6,725,425 | B1* | 4/2004 | Rajan | H04L 29/06027 |
| | | | | 707/E17.119 |
| 6,732,102 | B1* | 5/2004 | Khandekar | G06F 16/30 |
| | | | | 715/764 |
| 6,941,318 | B1 | 9/2005 | Tamayo et al. | |
| 7,103,838 | B1* | 9/2006 | Krishnamurthy | G06F 40/194 |
| | | | | 707/999.1 |
| 7,200,804 | B1* | 4/2007 | Khavari | G06F 16/951 |
| | | | | 707/E17.119 |
| 7,523,129 | B1* | 4/2009 | Bent | G06F 8/38 |
| | | | | 707/999.102 |
| 7,774,742 | B2 | 8/2010 | Gupta | G06Q 10/06 |
| | | | | 717/102 |
| 8,042,112 | B1* | 10/2011 | Zhu | G06F 16/951 |
| | | | | 707/706 |
| 9,171,080 | B2* | 10/2015 | Song | G06F 16/9535 |
| 11,030,691 | B2* | 6/2021 | Parmar | G06F 16/955 |
| 2003/0195889 | A1 | 10/2003 | Yao et al. | |
| 2004/0015784 | A1* | 1/2004 | Chidlovskii | G06F 16/972 |
| | | | | 715/255 |
| 2004/0172307 | A1* | 9/2004 | Gruber | G16H 10/60 |
| | | | | 705/3 |
| 2005/0022115 | A1* | 1/2005 | Baumgartner | G06F 16/9535 |
| | | | | 715/205 |
| 2005/0229151 | A1* | 10/2005 | Gupta | G06Q 10/06 |
| | | | | 717/101 |
| 2006/0242180 | A1* | 10/2006 | Graf | G06F 16/38 |
| 2007/0094060 | A1* | 4/2007 | Apps | G06F 16/2428 |
| | | | | 705/7.36 |
| 2007/0198727 | A1* | 8/2007 | Guan | G06F 16/84 |
| | | | | 709/201 |
| 2008/0027895 | A1* | 1/2008 | Combaz | G06F 16/335 |
| 2008/0091663 | A1* | 4/2008 | Inala | H04L 67/142 |
| 2009/0055727 | A1* | 2/2009 | Hansen | G06F 16/9577 |
| | | | | 709/206 |
| 2009/0132524 | A1* | 5/2009 | Stouffer | G06F 16/951 |
| | | | | 707/999.005 |
| 2010/0162097 | A1* | 6/2010 | Dalvi | G06F 40/143 |
| | | | | 715/234 |
| 2011/0145218 | A1* | 6/2011 | Meyerzon | G06F 16/9535 |
| | | | | 707/E17.014 |
| 2011/0185273 | A1* | 7/2011 | DaCosta | G06Q 99/00 |
| | | | | 715/234 |
| 2011/0258195 | A1* | 10/2011 | Welling | G06V 30/262 |
| | | | | 707/E17.09 |
| 2011/0307479 | A1* | 12/2011 | Yin | G06F 16/9535 |
| | | | | 707/E17.108 |
| 2012/0124086 | A1* | 5/2012 | Song | G06F 16/951 |
| | | | | 707/769 |
| 2013/0166207 | A1 | 6/2013 | Shao et al. | |
| 2013/0236111 | A1 | 9/2013 | Pintsov | |
| 2014/0172754 | A1 | 6/2014 | He et al. | |
| 2014/0359411 | A1* | 12/2014 | Botta | G06F 40/197 |
| | | | | 715/205 |
| 2015/0161257 | A1* | 6/2015 | Shivaswamy | G06F 16/951 |
| | | | | 707/709 |
| 2015/0199744 | A1* | 7/2015 | Tolvanen | G06F 16/9537 |
| | | | | 707/737 |
| 2016/0092458 | A1* | 3/2016 | Gottlob | G06F 16/958 |
| | | | | 715/230 |
| 2016/0092730 | A1 | 3/2016 | Smirnov et al. | |
| 2016/0188717 | A1 | 6/2016 | Rosenberg et al. | |
| 2016/0371603 | A1* | 12/2016 | A V | G06N 20/00 |
| 2017/0104841 | A1* | 4/2017 | Duke | G06F 16/245 |
| 2018/0018429 | A1* | 1/2018 | Rice | G06F 16/248 |
| 2018/0060495 | A1* | 3/2018 | Mahapatra | G16H 50/50 |
| 2018/0083901 | A1* | 3/2018 | McGregor, Jr. | H04L 51/10 |
| 2018/0150562 | A1 | 5/2018 | Gundimeda et al. | |
| 2019/0172586 | A1* | 6/2019 | Choksi | G16H 10/60 |
| 2019/0287171 | A1* | 9/2019 | Parmar | G06N 5/01 |
| 2020/0089712 | A1* | 3/2020 | Tripathi | G06F 16/951 |
| 2020/0210511 | A1* | 7/2020 | Korobov | G06F 16/957 |

OTHER PUBLICATIONS

Crescenzi, V. et al., "RoadRunner: Towards Automatic Data Extraction from Large Web Sites," 2001, 19 pages.*

Hsu, C-N. et al., "Generating Finite-State Transducers for Semi-Structured Data Extraction From the Web," (1998), Elsevier Science pp. 521-538.*

Arasu, A. et al., "Extracting Structured Data From Web Pages," (2003), ACM, pp. 337-348.*

Cho, J. et al., "Efficient Crawling Through URL Ordering," Computer Networks and ISDN Systems 30 (1998) 161-172.*

Hersovici, M. et al., "The Shark-Search Algorithm: An Application: Tailored Web Site Mapping," Computer Networks and ISDN Systems 30 (1998) 317-326.*

McCallum, A. et al., "Buidling Domain-Specific Search Engines with Machine Learning Techniques," 2009, 12 pages.*

Diligenti, M. et al., "Focused Crawling using Context Graphs," 26th International Conference on Very Large Databases, VLDB 2000, Cairo, Egypt, pp. 527-534, 2000.*

Shen, W. et al., "An Algorithm on Web Article Automatic Extraction Based on DOM Structure," International Journal of Hybrid Information Technology vol. 8, No. 3 (2015), pp. 243-254.*

Meng, X. et al., "A Supervised Visual Wrapper Generator for Web-Data Extraction," Proceedings of the 27th Annual International Computer Software and Applications Conference (Compsac'03) 2003, 6 pages.*

Papadakis, N. K. et al., "Stavies: A System for Information Extraction from Unknown Web Data Sources Through Automatic Web Wrapper Generation Using Clustering Techniques," IEEE Transactions on Knowledge and Data Engineering, vol. 17, No. 12, Dec. 2005, pp. 1638-1652.*

Liu, L. et al., "XRWAP: An XML-enabled Wrapper Construction System for Web Information Sources," (2000), 11 pages.*

Lin, L. et al., "Using Structured Tokens to Identify Webpages for Data Extraction," G. Dong et al. (Eds.): APWeb/WAIM 2007, LNCS 4505, pp. 241-252, 2007, Springer-Verlag Berlin Heidelberg 2007.*

Shete, D. et al., "Survey Paper on Web Content Extraction & Classification," 2021 6th International Conference for Convergence in Technology (I2CT) Pune, India. Apr. 2-4, 2021, IEEE, pp. 1-6.*

Uzun, E. et al.,"An Effective and Efficient Web Content Extractor for Optimizing the Crawling Process," Softw. Pract. Exper. 2014; 44:1181-1199.*

Liu, Yang et al. "Extracting Patient Demographics and Personal Medical Information from Online Health Forums." AMIA . . . Annual Symposium proceedings. AMIA Symposium 2014 (2014): 1825-34.*

Pol K. et al., "A Survey on Web Content Mining and Extraction of Structured and Semistructured Data," (2008_, IEEE, pp. 543-546.*

Bhargavi, P. et al., "Knowledge Extraction Using Rule Based Decision Tree Approach," IJCSNS International Journal of Computer Science and Network 296 Security, vol. 8 No. 7, Jul. 2008.*

Hong-ye, C., "Method of Web Information Extraction Based on Decision Tree," (2009), IEEE, 3 pages.*

Esposito, F. et al., "A Comparative Analysis of Method for Pruning Decision Trees," May 1997, IEEE, pp. 476-491.*

Yang, J. et al., "An Interface Agent for Wrapper-Based Information Extraction," 2005, Springer, pp. 291-302.*

Shah, P.B. et al., "Survery Based on DOM and Visual Ques for Extracting Structure Data From Web," (2015), IITRD, pp. 1-8.*

Kumar, A. et al., "Novel Self-Learning Based Crawling and Data Mining for Automatic Information Extraction," 2015, IEEE, pp. 732-738.*

Finch, D.K., "TagLine: Information Extraction for Semi-Structured Text Elements in Medical Progress Notes," Jan. 2012, Univ. of South Florida, 251 total pages.*

Safavian, S.R. et al., "A Survey of Decision Tree Classifier Methodology," (1991), IEEE, pp. 660-674.*

Taniguchi, K. et al., "Mining Semi-Structured Data by Path Expressions," (2001), Springer, pp. 378-388.*

Sigursson, K. et al., "Heritrix User Manual," (2004), Internet Archive, 57 pages.*

Girardi, C., Ricca, F. and Tonella, P. (2006), "Web crawlers com-

(56) References Cited

OTHER PUBLICATIONS pared", International Journal of Web Information Systems, vol. 2 No. 2, pp. 85-94.*

Shi, S. et al. NEXIR: A Novel Web Extraction Rule Language toward a Three-Stage Web Data Extraction Model. In: Lin, X., Manolopoulos, Y., Srivastava, D., Huang, G. (eds) Web Information Systems Engineering—WISE 2013. WISE 2013. Lecture Notes in Computer Science, vol. 8180. (Year: 2013).*

Furche, T., Gottlob, G., Grasso, G. et al. Oxpath: A language for scalable data extraction, automation, and crawling on the deep web. The VLDB Journal 22, 47-72 (2013). (Year: 2013).*

Ferrara, Emilio & De Meo, Pasquale & Fiumara, Giacomo & Baumgartner, Robert. (2012). Web Data Extraction, Applications and Techniques: A Survey. ACM Computing Surveys (Under Review). 70. 10.1016/j.knosys.2014.07.007. (Year: 2012).*

Baumgartner, R., Gatterbauer, W., Gottlob, G. (2009). Web Data Extraction System. In: Liu, L., Özsu, M.T. (eds) Encyclopedia of Database Systems. Springer, Boston, MA (Year: 2009).*

A. Schulz, J. Lässig and M. Gaedke, "Practical Web Data Extraction: Are We There Yet?—A Short Survey," 2016 IEEE/WIC/ACM International Conference on Web Intelligence (WI), Omaha, NE, USA, 2016, pp. 562-567 (Year: 2016).*

S. M. Meystre, G. K. Savova, K. C. Kipper-Schuler, and J. F. Hurdle, "Extracting information from textual documents in the electronic health record: a review of recent research," Yearb Med Inform, pp. 128-144, 2008. (Year: 2008).*

Kahn, Asad, Text-Mining and Analysis of the Doctor's Meta-data and Text-Reviews Using Topic-Modeling (LDA) Techniques, Sep. 2019, available Oct. 30, 2019, 115 total pages. (Year: 2019).*

Neustein, Amy & Imambi, S. & Teixeira, António & Ferreira, Liliana & Rodrigues, Mario. (2014). Application of Text Mining to Biomedical Knowledge Extraction: Analyzing Clinical Narratives and Medical Literature. (Year: 2014).*

Yoon Ho Cho, et al. "A personalized recommender system based on web usage mining and decision tree induction," Expert Systems with Applications, vol. 23, Iss. 3, 2002; https://doi.org/10.1016/S0957-4174(02)00052-0. (Year: 2002).*

International Search Report mailed Feb. 2, 2021 for Appl. No. PCT/US2020/58286, 3 pages.

The Written Opinion mailed Feb. 2, 2021 for Appl. No. PCT/US2020/58286, 8 pages.

Extended European Search Report directed to related European Application No. 20883009.1, mailed on Oct. 5, 2023, 8 pages.

* cited by examiner

High Priority
- States A, B, C, and D
- Regions Northeast, Mid-Atlantic, and Southwest
- Providers 1, 2, and 3

Moderate Priority
- States E, F, and G
- Region Northwest Pacific
- Providers 4, 5, and 6

Low Priority
- All remaining states
- All remaining regions
- All remaining providers

FIG. 4

| First Name | Last Name | Address | Phone Number | Email Address | Specialty | License No. | Expiration Date |
|---|---|---|---|---|---|---|---|
| John | Doe | 123 Maple Ave Somewhere, NJ 07005 | (973) 999-1234 | john.doe@doctor.org | Internal Medicine | 123456 | 12/22/2020 |
| Jane | Doe | 123 Maple Ave Somewhere, NJ 07005 | (973) 999-1234 | jane.doe@doctor.org | Internal Medicine | 123457 | 12/22/2020 |

FIG. 5

Plaintree Medical Referral

| Dentist | Address | Phone # |
|---------|---------|---------|
| John Doe | 123 Main St | 123-456-7890 |

Thank you for using our medical referral service. If you have any comment on how to improve our service please call 987-654-3210.

Plaintree Medical Referral

| Dentist | Address | Phone # |
|---------|---------|---------|
| John Doe | 123 Main St | 123-456-7890 |

954, 964, 952, 966, 956, 962, 900

Thank you for using our medical referral service. If you have any comment on how to improve our service please call 987-654-3210.

FIG. 9B

EFFICIENT CRAWLING USING PATH SCHEDULING, AND APPLICATIONS THEREOF

BACKGROUND

Field

This field is generally related to processing information.

Background

As technology advances, an ever-increasing amount of demographic information is becoming digitized. For example, for healthcare providers, demographic information may include, but is not limited, to their name, address, specialties, academic credentials, certifications, and the like. This demographic information may be available from various public data sources, such as websites. These websites may retrieve the demographic information from underlying databases, such as state, county, city, or municipality databases, that store the data. For example, states may have licensing boards that maintain lists of all licensed healthcare providers, along with their associated demographic information. In another example, health insurance companies may have public websites listing the healthcare providers, and associated demographic information, in their network. In another example, healthcare providers may themselves set up public websites that list such demographic information about their practices.

Some of these websites may be organized by trees of information. For example, to retrieve demographic information about a particular healthcare provider, a user may first select the county from a drop-down list. Then another page appears asking the user to select a town in the selected county from a drop-down list. Then, a third page may appear asking the user to select a health care specialty. Only then are the healthcare providers meeting the selected criteria displayed, along with at least some of the relevant demographic information stored in the underlying database.

Entities may have a need to maintain demographic information. For example, health insurance companies may have a need to maintain demographic information about healthcare providers that need to be reimbursed for claimed services. Often times this information may be inaccurate, or less accurate than information available from other public data sources.

To manually retrieve data from these public data sources would be difficult and time-consuming. Moreover, many of these data sources are not adapted to allow for automated retrieval of information. They are designed to provide human users the information when they are surfing the website. If an automated system hits these public data sources with too many requests in too short a time frame, it may cause the data source to overload and fail.

In addition, the returning data may not be structured in a known format. It may be presented in a way that, once rendered, a human user would readily be able to identify the demographic information and how it corresponds to a particular healthcare provider. However, because the data may not be in a known, standard format, an automated system may have difficulty parsing the data and associating the demographic information describing a single healthcare provider.

Thus, systems and methods are needed to improve extracting the demographic information from these data sources and consolidating the demographic information into a validated and up-to-date directory while reducing the burden on physicians and healthcare providers.

BRIEF DESCRIPTION OF THE DRAWINGS

The accompanying drawings, which are incorporated herein and form part of the specification, illustrate the present disclosure and, together with the description, further serve to explain the principles of the disclosure and enable a person skilled in the relevant art to make and use the disclosure.

FIG. 4 illustrates example priority levels assigned to the one or more data sources, according to aspects of the present disclosure.

FIG. 5 illustrates an example report generated by the system for accumulating data from the one or more data sources, according to aspects of the present disclosure.

FIGS. 9A-B illustrates a diagram illustrating how to extract geometric distances between page elements.

The drawing in which an element first appears is typically indicated by the leftmost digit or digits in the corresponding reference number. In the drawings, like reference numbers may indicate identical or functionally similar elements.

DETAILED DESCRIPTION

Embodiments provide ways to retrieve unstructured data along from data sources not optimized for automated retrieval. For example, embodiments may generate a branched tree for each data source that maps out paths to individual sites of, for example, a healthcare provider listing the unstructured data. Using this branched tree, tasks can be generated to navigate along a path with the data source to each site and extract the unstructured data from the data source. In this way, embodiments provide the ability to navigate through a site from a base site to a site that has the relevant data.

In some embodiments, the data requests are made in a prioritized, yet random nature. For example, the data sources may be categorized by priority (e.g., high priority, moderate priority, low priority, etc.), and the system may randomly select a data source within a given priority level and assign a task associated with the selected data source to one of the data extractors. Furthermore, the system may monitor the number of data extractors currently navigating a given data source to avoid overloading the data source, which may cause the data source to crash.

Finally, when the data site is reached, the data extracted may be unstructured. In other words, it may be in a markup language designed to render to a human user. However, the demographic information sought might not be tagged. That is, the markup language may not identify what data constitutes a name and associated telephone number or address. To deal with that, in some embodiments, the demographic information may be identified using, for example, a simple regular expression. Once the demographic information is identified, a distance between the respective fields is determined. The distance may be the geometric distance in the rendered page or distance between the two fields within the markup code. A model may be trained based at least in part on this data to predict whether the various pieces of extracted demographic information relate to the same person. In this way, embodiments may use machine learning to interpret automatically documents that are not formatted specifically for a machine.

In the detailed description that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Figure 1:
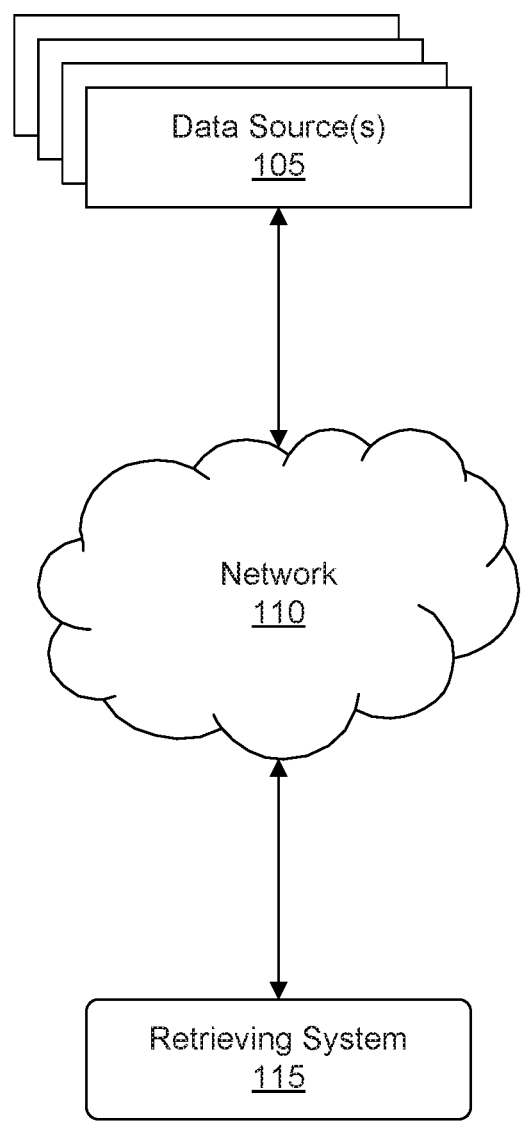
FIG. 1 illustrates a diagram of a network for communications between one or more data sources and a system, according to aspects of the present disclosure.

FIG. 1 is a diagram illustrating a system 100 for communications over a network 110 between one or more data sources 105 and a retrieving system 115. In some embodiments, the one or more data sources 105 may be a data source, such as a website, that includes demographic information of one or more individuals, such, as healthcare providers, including but not limited to, doctors, dentists, physician assistants, nurse practitioners, nurses, or the like. Although the present disclosure describes the individuals as being healthcare providers, it should be understood by those of ordinary skill in the arts that present disclosure may be implemented by accumulating data from any data source.

In some instances, the one or more data sources 105 may include a Center for Medicaid and Medicare (CMS) services data source, a directory data source, a Drug Enforcement Agency (DEA) data source, a public data source, a National Provider Identifier (NPI) data source, a registration data source, and/or a claims data source. The CMS data source may be a data service provided by a government agency. The database may be distributed and different agencies organizations may be responsible for different data stored in CMS data source. And CMS data source may include data on healthcare providers, such as lawfully available demographic information and claims information. CMS data source may also allow a provider to enroll and update its information in the Medicare Provider Enrollment System and to register and assist in the Medicare and Medicaid Electronic Health Records (EHR) Incentive Programs.

The directory data source may be a directory of healthcare providers. In one example, the directory data source may be a proprietary directory that matches healthcare providers with demographic and behavioral attributes that a particular client believes to be true. The directory data source may, for example, belong to an insurance company and can only be accessed and utilized securely with the company's consent.

The DEA data source may be a registration database maintained by a government agency such as the DEA. The DEA may maintain a database of healthcare providers, including physicians, optometrists, pharmacists, dentists, or veterinarians, who are allowed to prescribe or dispense medication. The DEA data source may match a healthcare provider with a DEA number. In addition, DEA data sources may include demographic information about healthcare providers.

The public data source may perhaps be a web-based data source such as an online review system. These data sources may include demographic information about healthcare providers, area of specialty, and behavioral information such as crowd sourced reviews.

The NPI data source may be a data source matching a healthcare provider to a NPI. The NPI is a Health Insurance Portability and Accountability Act (HIPAA) Administrative Simplification Standard. The NPI is a unique identification number for covered health care providers. Covered health care providers and all health plans and health care clearinghouses must use the NPIs in the administrative and financial transactions adopted under HIPAA. The NPI is a 10-position, intelligence-free numeric identifier (10-digit number). This means that the numbers do not carry other information about healthcare providers, such as the state in which they live or their medical specialty. NPI data source may also include demographic information about a healthcare provider.

The registration data source may include state licensing information. For example, a healthcare provider, such as a physician, may need to register with a state licensing board. The state licensing board may provide the registration data source information about the healthcare provider, such as demographic information and areas of specialty, including board certifications.

The claims data source may be a data source with insurance claims information. Like the directory data source, the claims data source may be a proprietary database. Insurance claims may specify information necessary for insurance reimbursement. For example, claims information may include information on the healthcare provider, the services performed, and perhaps the amount claimed. The services performed may be described using a standardized code system, such as ICD-9. The information on the healthcare provider could include demographic information.

However, the one or more data sources 105 may each have different formats for providing the demographic information of the healthcare providers and/or list different types of demographic information. As such, the demographic information of each healthcare provider may be inconsistent from one data source 105 to another. In some embodiments, the data sources 105 may be hosted on a server, such as a host server, a web server, an application server, etc., a data center device, or a similar device, capable of communicating via the network 110.

The network 110 may include one or more wired and/or wireless networks. For example, the network 110 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

Figure 2:
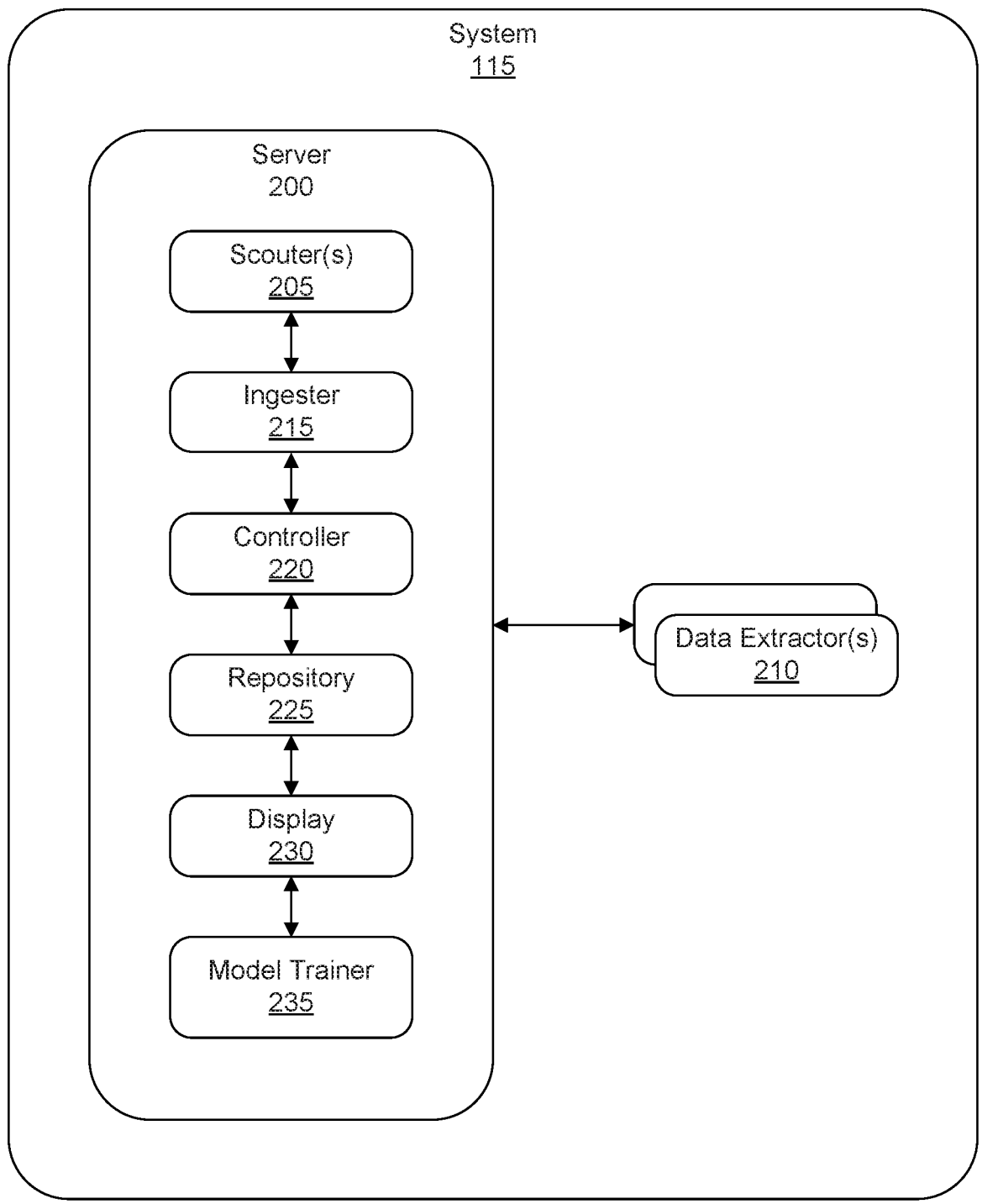
FIG. 2 illustrates a diagram of a system for accumulating data from the one or more data sources, according to aspects of the present disclosure.

To accumulate and store the demographic information from the data sources 105, the system 115 may include various components as illustrated in FIG. 2.

Turning to FIG. 2, system 115 includes a server 200 having one or more scouters 205, an ingester 215, a controller 220, a repository 225, a display 230, and a model trainer 235. System 115 also includes one or more data extractors 210.

In some embodiments, one or more scouters 205 may be configured to explore all possible permutations of each data source 105 to arrive at a site of each individual listed on the data source 105. To achieve this, model trainer 235 may be used to train the one or more scouters 205 using machine learning algorithms to iteratively navigate a respective data source 105 until reaching the site of each individual. For example, each scouter 205 may be trained to select a combination of one or more of a series of links, drop-down menus, radial buttons, etc., until a path to the site of each individual is determined. In some embodiments, the series of links, drop-down menus, etc. may include one or more parameters for searching for healthcare providers. The parameters may include a county, zip code, city, specialty, languages spoken, insurances accepted, and the like. It should be understood by those of ordinary skill in the arts that these are merely example parameters and that any combination of parameters may be used in accordance with aspects of the present disclosure.

In some embodiments, scouters 205 may be trained, for example, using supervised machine learning algorithms based on sample data sources to learn how to navigate the data sources to the sites of each individual. For example, using the sample data sources, the scouters 205 may be trained on how to select a combination of the one or more of a series of links, the drop-down menus, the radial buttons, etc. That is, the scouters 205 may be trained on set of training examples (e.g., sample data sources), such that the scouters 205 may navigate the data sources 105 without human intervention. An example of supervised machine learning algorithms that may be used to train the scouters 205 include, but are not limited to, support vector machines, linear regression, logistic regression, naive Bayes, linear discriminant analysis, decision trees, k-nearest neighbor algorithm, neural networks, and similarity learning. It should be understood by those of ordinary skill in the art that these are merely example supervised machine learning algorithms and that other supervised machine learning algorithms may be used in accordance with aspects of the present disclosure.

In some embodiments, one or more scouters 205 may generate a decision tree for a respective data source 105 that provides a route to the site of each individual. That is, the scouters 205 may generate a decision tree for each of a plurality of data sources with the decision tree comprising one or more paths to respective sites of the data source 205.

Figure 3:
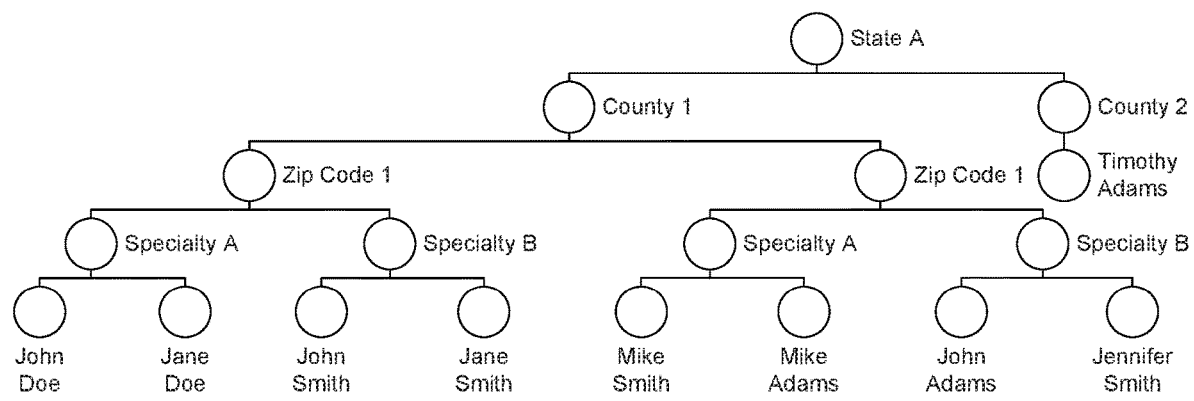
FIG. 3 illustrates an example decision tree generated by the system for accumulating data from the one or more data sources, according to aspects of the present disclosure.

As one example, FIG. 3 illustrates a decision tree for state A that includes the parameters county, zip code, and specialty. It should be understood that the parameters shown in FIG. 3 are merely example parameters, and that any combination and/or order of parameters may be used to navigate to the site of each individual.

Furthermore, in some instances, the decision tree may include multiple branches to the same site of an individual (i.e., fewer search parameters are required to reach the site of each individual), and in such instances, scouter 105 may retain the shortest path to the site of the individual while discarding all remaining paths to the site of the individual. Furthermore, scouter 205 may routinely survey the respective data source 105 to determine if any updates and/or modifications have been made (e.g., whether any healthcare providers have been added to/removed from the data source, whether the previous paths are still valid, whether any shorter paths have been established, etc.). For example, scouter 205 may survey a data source 105 for updates and/or modifications weekly, monthly, quarterly, etc. In some embodiments, the controller 220 may maintain a schedule for surveying data sources 105 and instruct scouter(s) 205 to survey data source 105 accordingly.

Using the decision tree generated by one or more scouters 205, controller 220 may generate and maintain a list of tasks for each of the plurality of data sources 205. In some embodiments, each task may correspond to a respective one of the one or more paths to navigate from a base web site to a destination, leaf web site that includes the desired demographic information. Each task may also include instructions for extracting demographic information from the respective site. That is, controller 220 may split the decision tree into separate tasks having instructions for obtaining the demographic information from the site of each individual. In some embodiments, controller 220 may communicate these tasks to a corresponding data extractor 210, with the task providing the corresponding data extractor 210 with instructions on how to extract the demographic information from the respective site. For example, controller 220 may assign and transmit the task to the corresponding data extractor. As another example, the controller 220 may store the tasks in a queue such that the data extractor 210 may select one of the tasks from the queue. The task communicated to the data extractor 210 may cause the data extractor 210 to navigate the corresponding data source to the respective site and extract the demographic information from the respective site. Furthermore, controller 220 may track which tasks have been communicated to data extractors 210 in order to ensure that data extractors 210 avoid performing duplicate tasks. In some embodiments, one or more data extractors 210 may be a computing device, such as a mobile phone (e.g., a smart phone, a radiotelephone, etc.), a laptop computer, a tablet computer, a handheld computer, or a similar type of device.

The instructions may include instructions for navigating through data source 105 to the respective site. For example, the instructions may indicate which link(s) to click, which drop-down option(s) to select, which radial button(s) to select, or the like, in order to navigate to the respective site. To achieve this, the instructions may also include instructions for emulating movements of a user when navigating the data source 105. That is, the instructions may indicate where to move the mouse on a given site to make the aforementioned selections. Additionally, the instructions may include instructions to move the mouse after clicking the particular link, selecting an option of the drop-down list, selecting a radial button, or the like. Further embodiments may include instructions for obviating a challenge-response test (e.g., a completely automated public Turing test to tell computers and humans apart "CAPTCHA"). For example, the instructions may direct the data extractor 210 to access a specific uniform resource locator ("URL"), rather than navigating through the data source 105. In some embodiments, the instructions for navigating through data source 105 may include instructions that cause the data extractor 205 to automatically navigate to a given page, e.g., a "Contact Us" page, of the data source 105 and extract the demographic information from the given site.

In some embodiments, the controller 220 may communicate the tasks to the data extractors 210 based on a combination of a priority level of a data source 105 and a random selection. To achieve this, the data sources 105 may be assigned a priority level. For example, as illustrated in FIG. 4, the data sources 105 may be assigned a high priority, a moderate priority, or a low priority.

As illustrated in FIG. 4, the priority levels may be assigned to different states, different regions, different insurance providers, etc. It should be understood by those of ordinary skill in the arts that these are merely example priority levels, and that any number of priority levels are further contemplated in accordance with aspects of the present disclosure. In some embodiments, for any given priority level, the controller 220 may communicate the tasks from a randomly selected data source 105 within a given priority level to corresponding data extractors 210. In some embodiments, the priority level for each data source 105 may be set by an administrator of the system 115 and may be adjusted any time.

The controller 220 may manage the number data extractors performing tasks for a corresponding data source 105. For example, in some embodiments, managing the number data extractors may include managing a maximum number of data extractors 210 performing tasks on each of the plurality of data sources 105. That is, to avoid overloading the data source 105, the controller 200 may limit the number of data extractors 210 performing tasks on a given data source 105. When the maximum number of data extractors for a given data source 105 is reached, the controller 220 may communicate task(s) of another data source 105 having the same priority level to a corresponding data extractor(s) 210. Additionally, or alternatively, when the maximum number of data extractors for a given data source is reached, the controller 220 may communicate task(s) of another data source 105 having a different priority level to a corresponding data extractor(s) 210. In some embodiments, the other data source 105 of the same or different priority level may be randomly selected.

In further embodiments, managing the number data extractors may include periodically adjusting the number of data extractors 210 performing tasks on a data source 105 to increase or decrease the workload on the data source 105. For example, the controller 220 may periodically adjust the number of data extractors 210 performing tasks on a data source 105 in order to avoid overloading the data source 105 or to maximize the load on data source 105 during off-peak usage hours (e.g., overnight). In some embodiments, after reducing the number of data extractors 210 performing tasks on data source 105, controller 220 may reassign data extractors 210 to perform tasks on another data source 105 having the same priority level. Additionally, or alternatively, controller 220 may reassign the data extractors 210 to perform tasks on another data source 105 having a different priority level. In some embodiments, the other data source 105 of the same or different priority level may be randomly selected.

In some embodiments, controller 220 may also generate a user interface presented on a display 230. For example, the user interface may indicate a color code indicator of the priority level of a data source 105, the number of tasks for each data source 105, an identification number of data source 105, the number of data extractors 210 performing tasks on each data source 105, a progress indicator of the tasks for each data source 105 (e.g., a percentage of jobs completed, whether data extractors 210 have started or completed the tasks, etc.), and an overall status of the tasks (e.g., "none," "executing," "initialized," "completed," etc.).

Using the user interface, an administrator may pause one or more data extractors 210 performing tasks on data source 105 and/or change the priority level of a data source 105. In some embodiments, the user interface may be updated in predetermined intervals, e.g., every 15 minutes, every hour, etc.

In further embodiments, controller 220 may also maintain a schedule for each data source 105 indicating when data source 105 should be crawled in order to obtain the demographic information. For example, each data source 105 may be crawled based on its own respective schedule (e.g., daily, weekly, bi-weekly monthly, bi-monthly, quarterly, etc.). Using these schedules, controller 220 may determine whether to obtain the demographic information from a specific site of a given data source 105. For example, when given data source 105 is scheduled for crawling, controller 220 may communicate a message to one of data extractors 210 with a script for exploring the data source 105. After a job is completed, controller 220 may receive a message from data extractor 210 indicating that the job is complete and also requesting a new job.

In some situations, data extractor 210 performing a given task may encounter a failure at data source 105 (e.g., data source 105 itself or the site of each individual is inaccessible). To resolve this, the script may include instructions for repeating the task when data extractor 210 encounters the failure. For example, the instructions may cause data extractor 210 to iteratively attempt to access the site of an individual at a set interval and for a set number of attempts (e.g., every twenty-four hours for three days). If data extractor still encounters the failure, the instructions may cause data extractor 210 to notify the controller 220 indicating such, and in response, controller 220 may dispatch scouter 205 to determine another path to the site of the individual, determine if the site of each individual is no longer active, or determine if the data source 105 itself is inaccessible.

In some embodiments, data extractors 210 may be trained using machine learning algorithms to accumulate unstructured demographic data from data sources 105 in a structured manner. For example, trainer 235 may be used to train data extractors 210, for example, using supervised machine learning algorithms to learn, identify, and extract the unstructured data on any given site. For example, using the sample data sources, data extractors 210 may identify a distance between two or more parameters, e.g., a name and address of a healthcare provider on a rendered image of given site of the data source. For example, the distance between the two or more parameters may be a vertical distance (e.g., the parameters are vertically aligned) or a horizontal distance (e.g., the parameters are vertically aligned). As another example, the distance between the two parameters may be the distance between x-y coordinates of each parameter in a rendered image of the site. In other words, in some embodiments, the distance between two parameters may be a spatial distance. It should be understood by those of ordinary skill in the art that the name and address are merely examples of demographic information, and that data extractors 210 may be trained to identify other types and combinations of demographic information. As another example, data extractors 210 may be trained to identify a number of pairs of parameters on a given site of data source 105. That is, in some situations, multiple healthcare providers may be listed on the same site with common demographic information or unique demographic information associated with each healthcare. In further embodiments, data extractors 210 may be trained to identify a ratio between a number of healthcare and a number of pieces of demographic information. As a further example, data extractors 210 may be trained to identify the demographic information based on a code used to generate the site. For example, data extractors 210 may identify the distance between the demographic information in marked-up language (e.g., XML or Hypertext Markup Language (HTML) code) on any given site. For example, the code for any each site may include nested node or trees, and the distance between the demographic information the node may be a number of steps between the nested code or tree of the different types of demographic information. Additionally, data extractors 210 may identify line number and character number of each of the parameters and determine a distance between them.

Data extractors 210 may be trained to identify whether the various pieces of demographic information are related to one another. For example, the distances, number of pairs of parameters, and/or ratio between a number of healthcare and a number of pieces of demographic information may be features inputted to generate a model. Trainer 235 may use a sample set generated by humans identifying related demographic information on the same page or by analyzing a sample set of pages with known positions or labeling of related demographic information. The labeling may be, for example, within tags in the markup language.

Using this training, data extractors 210 may identify any combination of demographic information on each respective site of a data source 105. That is, data extractors 210 may be trained on set of training examples (e.g., sample data sources), such that data extractors 210 may identify and extract the unstructured data on any given site without human intervention. Example supervised machine learning algorithms that may be used to train scouters 205 include, but are not limited to, support vector machines, linear regression, logistic regression, naive Bayes, linear discriminant analysis, decision trees, k-nearest neighbor algorithm, neural networks, and similarity learning. It should be understood by those of ordinary skill in the art that these are merely example supervised machine learning algorithms and that other supervised machine learning algorithms may be used in accordance with aspects of the present disclosure.

After identifying and extracting the unstructured demographic data, the data extractors 210 may reformat the demographic data in a structure manner. For example, as illustrated in FIG. 5, the data extractors 210 may generate a report having the data retrieved from the sites in a table format.

In the example, shown in FIG. 5, the structured format may include first name, last name, address, phone number, email address, specialty, license number, and expiration date. It should be understood by those of ordinary skill the art that this is merely an example report and that reports having different types of demographic information may be generated in accordance with aspects of the present disclosure. In some embodiments, the data extractors 210 may transmit the report to the server 200, which may then process the report. For example, the ingester 215 may be retrieve the demographic data from the report of the data extractors 210 and to separate the demographic information based on the category of data (e.g., name, address, phone, specialty, etc.) into separate databases within the repository 225. For example, the different categories of data may be separated into logical partitions within the repository 225. Alternatively, the different categories of data may be separated into different memories within the repository 225. In other words, the ingester 215 retrieves all of the demographic data accumulated for a given data source 105, identifies and categorizes the various pieces of information collected based on a category of data, and stores the categorized data within an assigned partition or database within the repository 225. In further embodiments, the ingester 215 may monitor each data source 105 to determine whether data relating to any individual has changed and requires updating.

Figure 6:
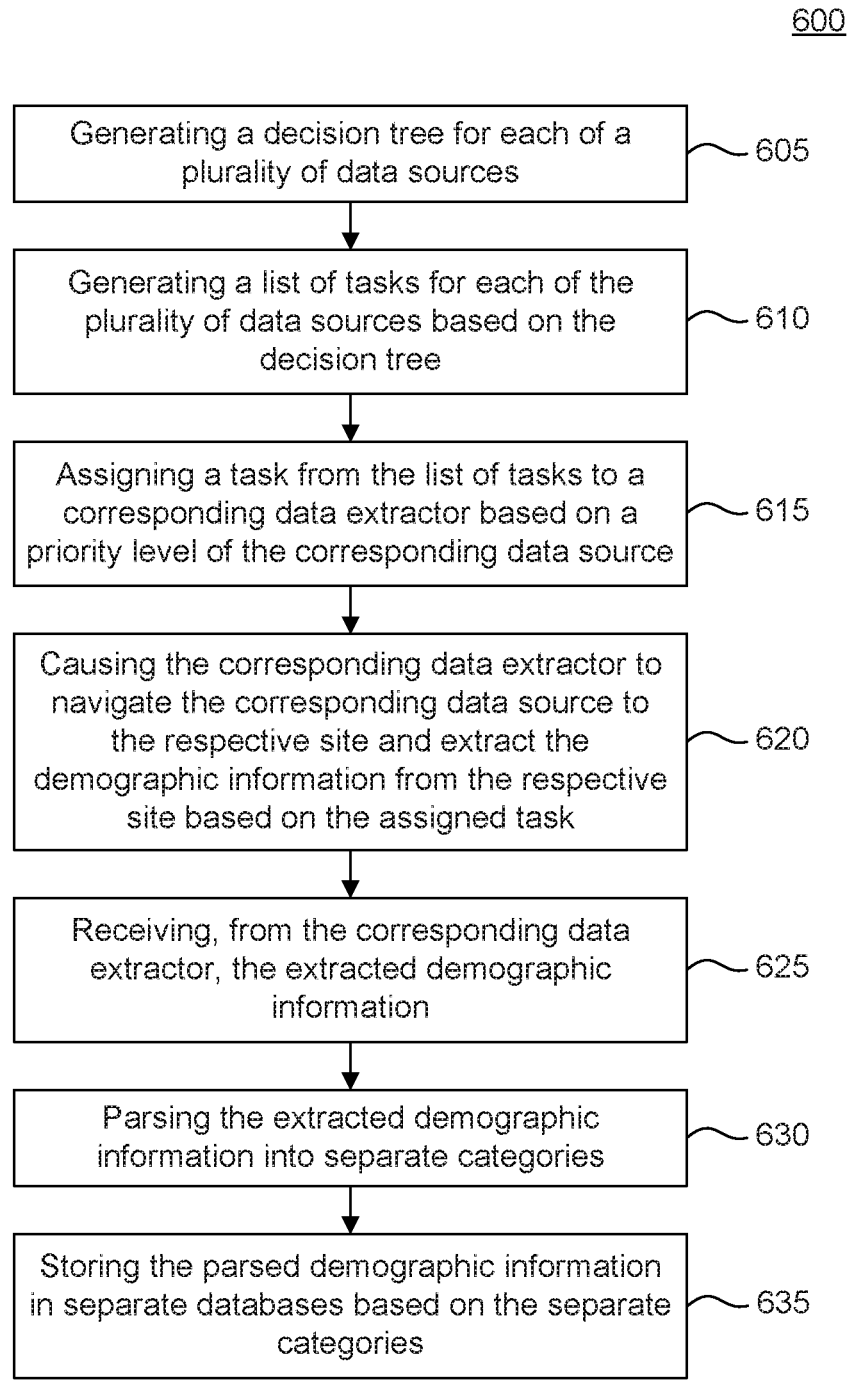
FIG. 6 illustrates a method of extracting unstructured data from a plurality of data sources, according to aspects of the present disclosure.

FIG. 6 illustrates a method of extracting unstructured data from a plurality of data sources, according aspects of the present disclosure. For example, a method 600 may include generating a decision tree for each of a plurality of data sources 605. The decision tree may comprise one or more paths to respective sites of the data source. For example, one or more scouters (e.g., the scouters 205 of FIG. 2) may be configured to explore all possible permutations of each data source (e.g., data sources 105 of FIG. 1) to arrive at a site of each individual listed on the data source. This may include selecting a combination of one or more of a series of links, drop-down menus, radial buttons, etc., until a path to the site of each individual is determined.

The method 600 may also include generating a list of tasks for each of the plurality of data sources (e.g., data sources 105 of FIG. 1) based on the decision tree 610. Each task may correspond to a respective one of the one or more paths and may comprise instructions for extracting demographic information from the respective site. For example, a controller (e.g., the controller 220 of FIG. 2) may split the decision tree into separate tasks having instructions for obtaining the demographic information from the site of each individual. The method 600 may also include communicating a task from the list of tasks to a corresponding data extractor based on a priority level of the corresponding data source 615. For example, the controller (e.g., the controller 220 of FIG. 2) may assign these tasks to a corresponding data extractor (e.g., the data extractor 210 of FIG. 2). As another example, the controller may store the tasks in a queue such that the data extractor may select one of the tasks from the queue. The task may provide the corresponding data extractor with instructions on how to extract the demographic information from the respective site.

The method 600 may also include causing the corresponding data extractor to navigate the corresponding data source to the respective site and extract the demographic information from the respective site based on the communicated task 620. For example, the communicated task may cause the corresponding data extractor (e.g., the data extractor 210 of FIG. 2) to navigate the corresponding data source to the respective site and extract the demographic information from the respective site based on the communicated task. The method 600 may also include receiving the extracted demographic information 625 from the corresponding data extractor. For example, the corresponding data extractor (e.g., the data extractor 210 of FIG. 2) may transmit the extracted data to a server (e.g., the server 200 of FIG. 2).

The method 600 may further include parsing the extracted demographic information into separate categories 630 and storing the parsed demographic information in separate databases based on the separate categories 635. For example, an ingester (e.g., ingester 215 of FIG. 2) may be configured to retrieve the demographic data accumulated by the data extractors (e.g., the data extractor 210 of FIG. 2) and separate the demographic information based on the category of data (e.g., name, address, phone, specialty, etc.) into separate databases within a repository (e.g., the repository 225 of FIG. 2). In some embodiments, the different categories of data may be separated into logical partitions within the repository (e.g., the repository 225 of FIG. 2). Alternatively, the different categories of data may be separated into different memories within the repository (e.g., the repository 225 of FIG. 2).

Each of the servers and modules described above can be implemented in software, firmware, or hardware on a computing device. A computing device can include but is not limited to: a personal computer, a mobile device such as a mobile phone, workstation, embedded system, game console, television, set-top box, or any other computing device. Further, a computing device can include, but is not limited to, a device having a processor and memory, including a non-transitory memory, for executing and storing instructions. The memory may tangibly embody the data and program instructions in a non-transitory manner. Software may include one or more applications and an operating system. Hardware can include, but is not limited to, a processor, a memory, and a graphical user interface display. The computing device may also have multiple processors and multiple shared or separate memory components. For example, the computing device may be a part of or the entirety of a clustered or distributed computing environment or server farm.

Figure 7:
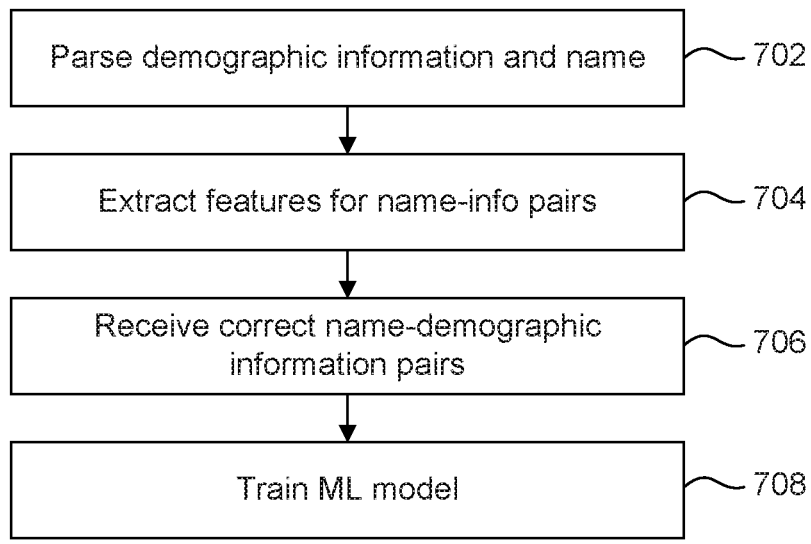
FIG. 7 illustrates a method of training a computing device to extract unstructured data from a plurality of data sources, according to aspects of the present disclosure.

FIG. 7 illustrates a method 700 of training a computing device to extract unstructured data from a plurality of data sources, according aspects of the present disclosure.

Method 700 starts in step 702 by person demographic information. The page may be represented in a markup language. One such example markup language is illustrated in FIG. 9A

FIG. 9A shows an example page 900 providing information about a healthcare provider as part of a medical referral service. In this example, page 900 may be represented by markup language such as HTML. Below is an example HTML snippet that may be used to represent the contents of page 900:

```
<!DOCTYPE HTML>
<html>
<head>
<title>Plaintree Medical Referral</title>
</head>
<body>
<tbody>
<tr><th>Dentist</th><th>Address</th><th>Phone #</th></tr>
<tr><td>John Doe</td><td>123 Main Street</td><td>123-456-7890</td></tr>
</tbody>
<p>Thank you for using our medical referral service. If you have any comments
on how to improve our service please call 987-654-3210.</p>
</body>
</html>
```

Returning to step 702, demographic information may be parsed from either the rendered page 900 or from the underlying markup language illustrated in the code snippet above. In different examples, regular expressions, or another set of rules, may be used to identify the phone numbers or addresses. Alternatively, machine learning classifiers may be used to identify these various fields in the markup language or in the rendered page (for example, using computer vision techniques). The different regular expressions or classifiers may each be configured to identify a particular type of demographic information, for example, name, address, or phone number.

Next, at step 704, a set of features is extracted based on the page and the identified demographic information. The set of features may include, for example, the number of data fields extracted, the number of different types of data fields extracted, and/or the ratio of names extracted to another type of information extractors, such as addresses. In addition, the set of features may include a distance between the various pieces of demographic and other information. The distance may include a geometric distance and/or a distance within the markup code.

How a geometric distance may be determined is illustrated in FIGS. 9A and 9B. As described above, FIG. 9A shows a page 900 illustrating a rendering of the marked up document. Such a rendering can be generated for example using WebKit or other browser package. As illustrated in FIG. 9B, a location is determined where each of the plurality of fields is located. In FIG. 9B, the fields are located at position 952, 954, 956, and 958. A name is detected at position 952, an address is detected at position 954, and phone numbers are detected at positions by 956 and 958. Such detection may be done by retrieving information from the rendering engine. In this embodiment, the rendering engine may provide locations of the respective fields. Alternatively, computer vision techniques may be used on the rendered page to determine the locations of the respective fields.

Once the location is determined, a geometric distance between the respective locations of the plurality of fields in the rendered marked-up document is calculated. In one embodiment, a distance is calculated for every pair of fields. In another embodiment, a distance is calculated between each name and each other type of demographic information. In FIG. 9B, a distance 964 is determined between fields 952 and 954. A distance 966 is determined between field 952 and 956. And a distance 962 is determined between fields 952 and 958.

The geometric distance may be an advantageous feature to use in the model because page 900 may be designed to present the demographic information to a human user in a way that the human user recognizes that the various demographic information represents a single healthcare provider. As illustrated in the example in FIG. 9B, a distance 962 between fields 952 and 958 is larger than a distance 966 between fields 952 and 956, suggesting that fields 952 and 956 represent demographic information from the same individual, while fields 952 and 958 do not.

In addition to or an alternative to the geometric distance, a distance within the markup code may be determined. In one embodiment, the distance may simply be the number of lines or characters of code between fields. In another embodiment, the distance may be a number of nodes separating the fields within a document object model, as illustrated, for example, in FIG. 10.

Figure 10:
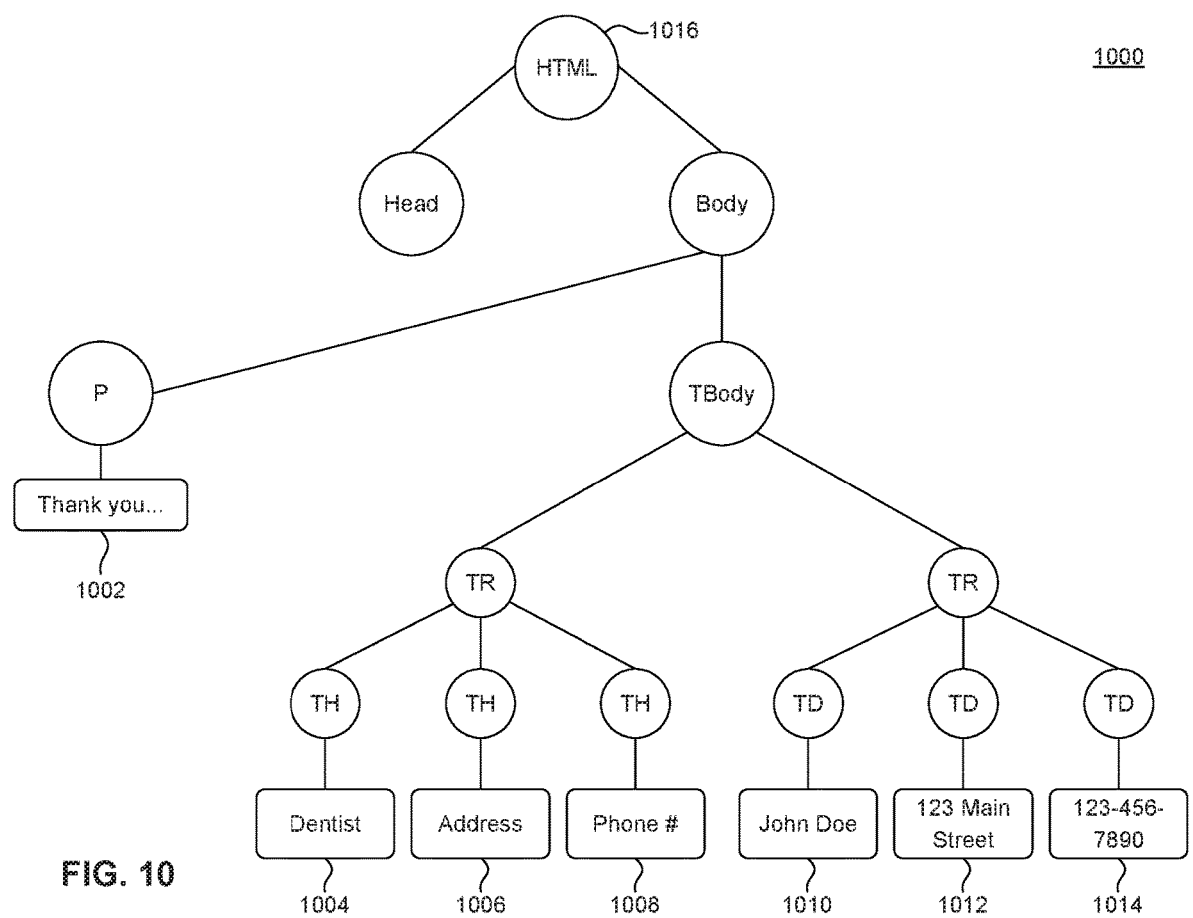
FIGS. 10-12 illustrate diagrams illustrating how to extract distances between fields in a markup language.

FIG. 10 illustrates a document object model 1000. The document object model may include a plurality of interconnected nodes. The plurality of interconnected nodes may, for example, be structured as a tree. For example, document object model 1000 has a root node 1016 and a number of leaf nodes 1002, 1004, 1006, 1008, 1010, 1012, and 1014 connected by intermediate nodes. Together, these nodes define the contents and format of the page. The various fields of demographic information are embedded within contents of some, but not all, of the leaf nodes.

Figure 11:
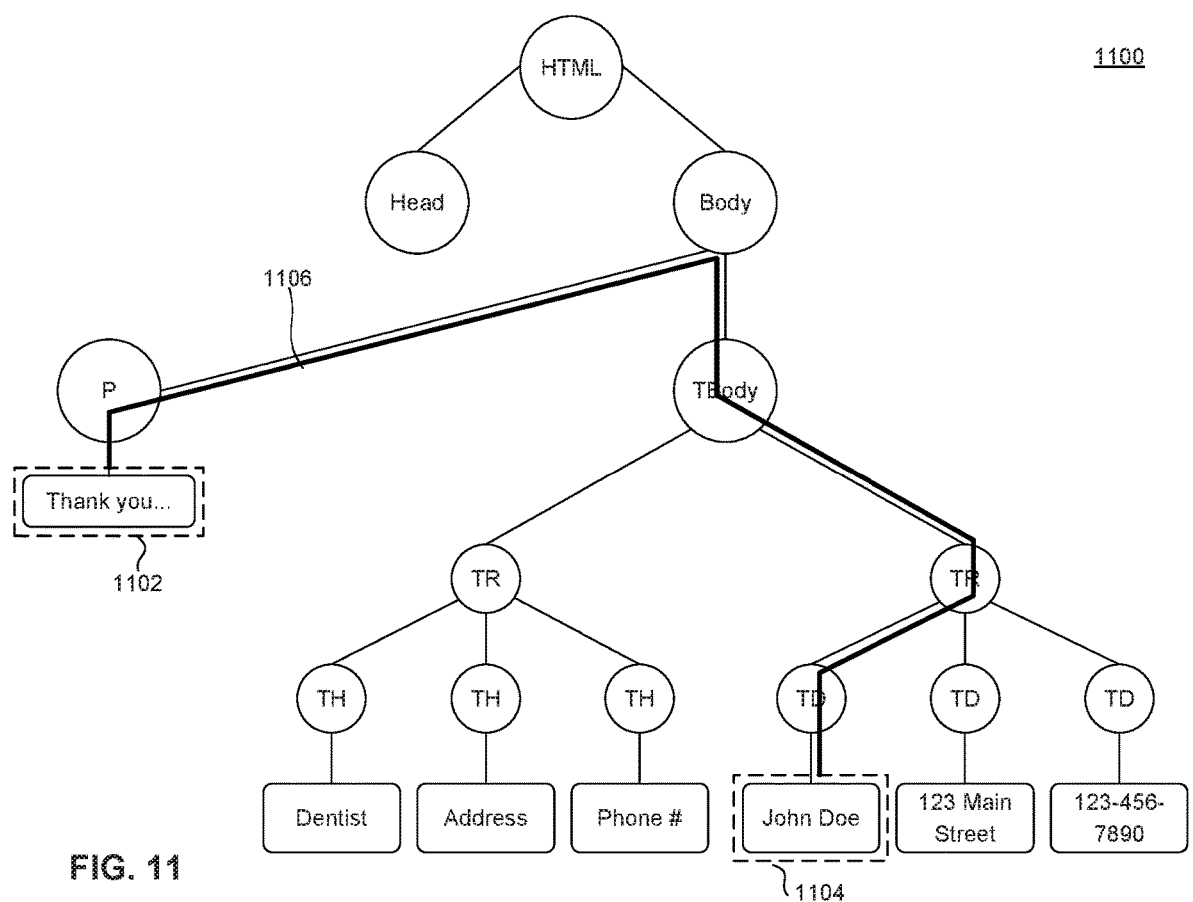
Figure 12:
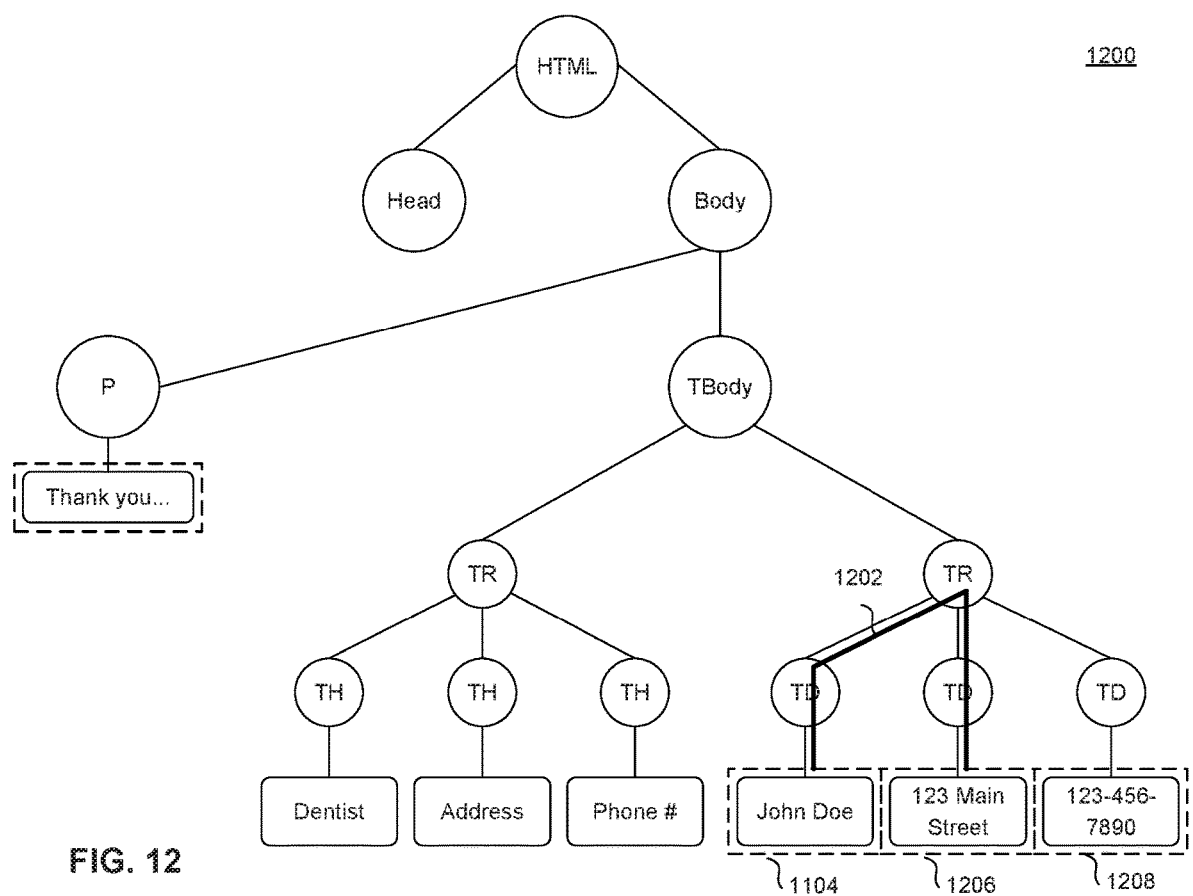

To determine the distance within the various fields of document object model 1000, where each of the plurality of fields is located in the document object model must be determined. As illustrated in FIGS. 11 and 12, leaf nodes 1102, 1104, 1206, and 1208 have demographic information.

Once the nodes having demographic information are identified, a distance between them in the document object model is determined. The distance may be determined by calculating the number of hops between the respective locations of the plurality of fields in the rendered marked-up document.

After the features are extracted, the method includes the correct groupings of demographic information representing a single healthcare provider on a page are received at step 706. The groupings may be identified by human user. Alternatively, the groupings may be generated given a known labeling of the demographic information on certain pages.

Finally, using the received groupings and extracted features, a machine learning model is trained at step 708.

Figure 8:
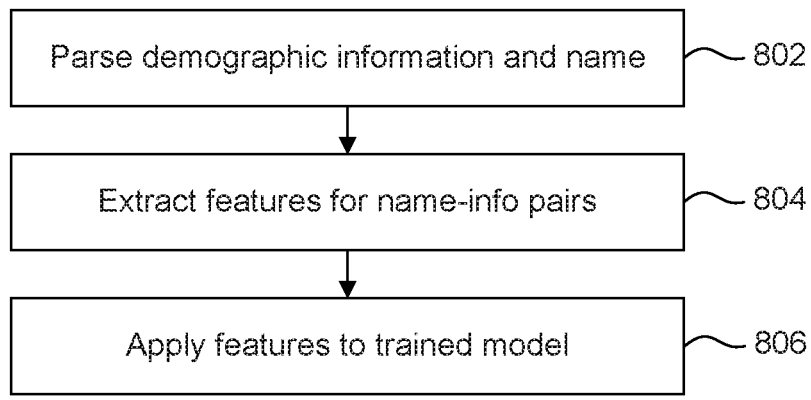
FIG. 8 illustrates a method of using a machine learning model.

FIG. 8 illustrates a method 800 of using a machine learning model. In FIG. 8, demographic information is parsed at step 802, as described above for step 702. Features are extracted at step 804, again as described above for step 704. At step 806, those features are applied to the model, which is trained to determine whether any two or more fields of demographic information represent the same individual healthcare provider based on the features provided. In this way, embodiments can identify fields of demographic information on page information that represent the same individual or provider.

Figure 13:
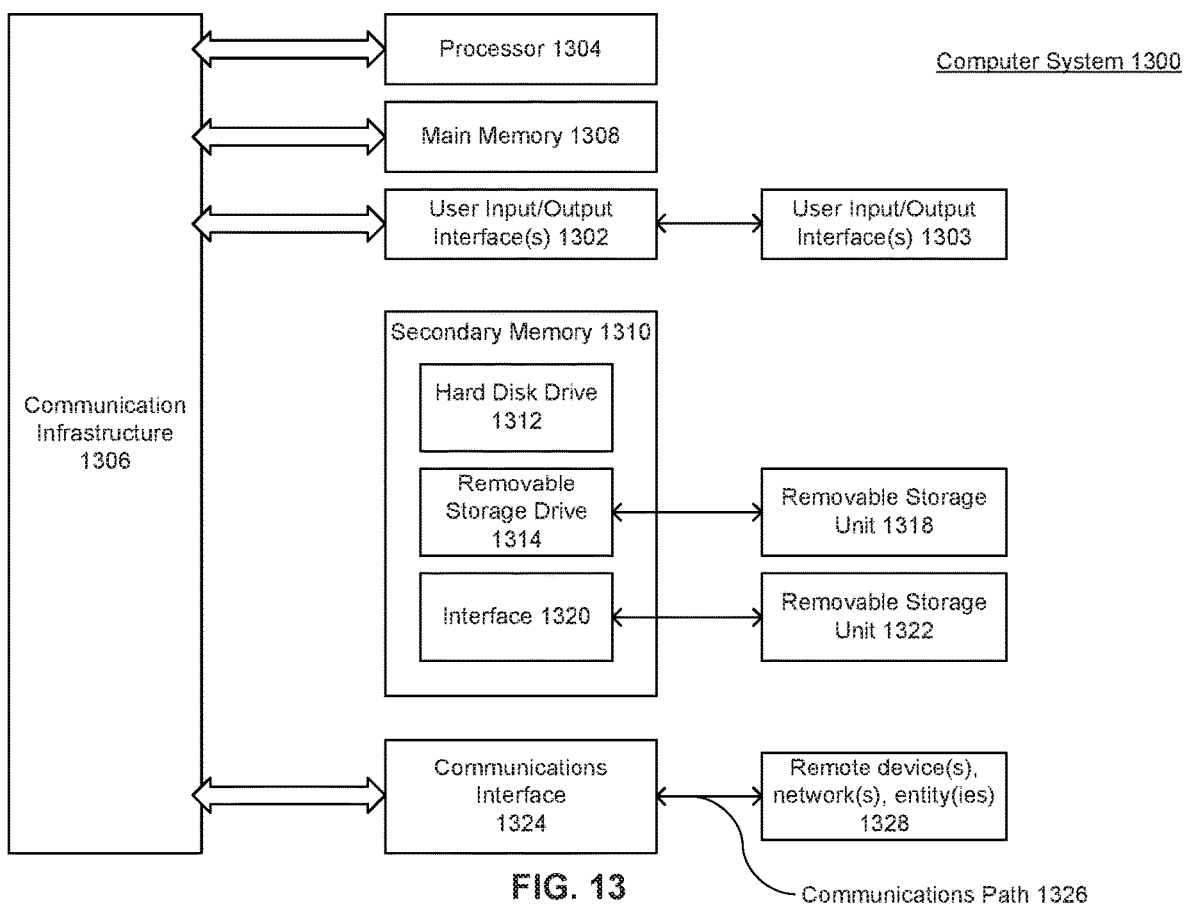
FIG. 13 is an example computer system useful for implementing various embodiments.

Various embodiments may be implemented, for example, using one or more well-known computer systems, such as computer system 1300 shown in FIG. 13. One or more computer systems 1300 may be used, for example, to implement any of the embodiments discussed herein, as well as combinations and sub-combinations thereof.

Computer system 1300 may include one or more processors (also called central processing units, or CPUs), such as a processor 1304. Processor 1304 may be connected to a communication infrastructure or bus 1306.

Computer system 1300 may also include user input/output device(s) 1303, such as monitors, keyboards, pointing devices, etc., which may communicate with communication infrastructure 1306 through user input/output interface(s) 1302.

One or more of processors 1304 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 1300 may also include a main or primary memory 1308, such as random access memory (RAM). Main memory 1308 may include one or more levels of cache. Main memory 1308 may have stored therein control logic (i.e., computer software) and/or data.

Computer system 1300 may also include one or more secondary storage devices or memory 1310. Secondary memory 1310 may include, for example, a hard disk drive 1312 and/or a removable storage device or drive 1314. Removable storage drive 1314 may be a floppy disk drive, a magnetic tape drive, a compact disk drive, an optical storage device, tape backup device, and/or any other storage device/drive.

Removable storage drive 1314 may interact with a removable storage unit 1318. Removable storage unit 1318 may include a computer usable or readable storage device having stored thereon computer software (control logic) and/or data. Removable storage unit 1318 may be a floppy disk, magnetic tape, compact disk, DVD, optical storage disk, and/any other computer data storage device. Removable storage drive 1314 may read from and/or write to removable storage unit 1318.

Secondary memory 1310 may include other means, devices, components, instrumentalities or other approaches for allowing computer programs and/or other instructions and/or data to be accessed by computer system 1300. Such means, devices, components, instrumentalities or other approaches may include, for example, a removable storage unit 1322 and an interface 1320. Examples of the removable storage unit 1322 and the interface 1320 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 1300 may further include a communication or network interface 1324. Communication interface 1324 may enable computer system 1300 to communicate and interact with any combination of external devices, external networks, external entities, etc. (individually and collectively referenced by reference number 1328). For example, communication interface 1324 may allow computer system 1300 to communicate with external or remote devices 1328 over communications path 1326, which may be wired and/or wireless (or a combination thereof), and which may include any combination of LANs, WANs, the Internet, etc. Control logic and/or data may be transmitted to and from computer system 1300 via communication path 1326.

Computer system 1300 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 1300 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 1300 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 1300, main memory 1308, secondary memory 1310, and removable storage units 1318 and 1322, as well as tangible articles of manufacture embodying any combination of the foregoing. Such control logic, when executed by one or more data processing devices (such as computer system 1300), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 13. In particular, embodiments can operate with software, hardware, and/or operating system embodiments other than those described herein.

CONCLUSION

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computer-implemented method for extracting data from a plurality of data sources, comprising:
   generating a decision tree for a data source of the plurality of data sources, wherein the decision tree comprises a base website at a root node and a plurality of respective sites represented as corresponding leaf nodes of the decision tree, wherein the decision tree specifies one or more paths to navigate from the base website to the plurality of respective sites containing unstructured demographic data for a healthcare provider, wherein each of the plurality of respective sites and the corresponding leaf nodes of the decision tree represent a step in the decision tree, wherein a respective site is a website accessible from the base website of the data source;
   generating, based on the decision tree, a list of tasks corresponding to each of the plurality of data sources, wherein each task includes instructions for how to extract the unstructured demographic data corresponding to the respective site corresponding to one of the one or more paths;
   generating a user interface to be presented on a display, wherein the user interface indicates the list of tasks to be performed for each of the plurality of data sources and a status for the list of tasks;
   navigating, based on the decision tree, within a corresponding data source from the base website to the respective site as specified by a specified path, wherein the specified path is a plurality of steps to navigate from the base website to the respective site where the unstructured demographic data is located;
   parsing the unstructured demographic data from the respective site into separate categories;
   storing the parsed unstructured demographic data in separate databases based on the separate categories; and
   generating a report based on the parsed unstructured demographic data that displays the parsed unstructured demographic data in a structured format.

2. The method of claim 1, wherein the navigating comprises iteratively accessing the respective site for a predetermined number of attempts when the corresponding data source or the respective site is initially inaccessible.

3. The method of claim 2, further comprising receiving an error notification when the corresponding data source or the respective site is inaccessible after completing the predetermined number of attempts.

4. The method of claim 1, wherein the user interface further indicates a color code indicator of a priority level of each of the plurality of data sources.

5. The method of claim 1, further comprising managing a plurality of data extractors performing tasks on each of the plurality of data sources.

6. The method of claim 5, wherein managing the plurality of data extractors comprises managing a maximum number of data extractors performing tasks on each of the plurality of data sources.

7. The method of claim 6, wherein when the maximum number of data extractors for a first data source of the plurality of data sources is reached, the method further comprises assigning tasks of a second data source of the plurality of data sources having a same priority level as the first data source.

8. The method of claim 6, wherein when the maximum number of data extractors for a first data source is reached, the method further comprises assigning tasks of a second data source of the plurality of data sources having a different priority level as the first data source.

9. The method of claim 5, wherein managing the plurality of data extractors comprises periodically adjusting the plurality of data extractors performing tasks on the corresponding data source.

10. A non-transitory program storage device having instructions stored thereon that, when executed by at least one computing device, causes the at least one computing device to perform a method, the method comprising:
    generating a decision tree for a data source of a plurality of data sources, wherein the decision tree comprises a base website at a root node and a plurality of respective sites represented as corresponding leaf nodes of the decision tree, wherein the decision tree specifies one or more paths to navigate from the base website to the plurality of respective sites containing unstructured demographic data for a healthcare provider, wherein each of the plurality of respective sites and the corresponding leaf nodes of the decision tree represent a step in the decision tree, wherein a respective site is a website accessible from the base website of the data source;

generating, based on the decision tree, a list of tasks corresponding to each of the plurality of data sources, wherein each task includes instructions for how to extract the unstructured demographic data corresponding to the respective site corresponding to one of the one or more paths;

generating a user interface to be presented on a display, wherein the user interface indicates the list of tasks to be performed for each of the plurality of data sources and a status for the list of tasks;

navigating, based on the decision tree, within a corresponding data source from the base website to the respective site as specified by a specified path, wherein the specified path is a plurality of steps to navigate from the base website to the respective site where the unstructured demographic data is located;

parsing the unstructured demographic data from the respective site into separate categories;

storing the parsed unstructured demographic data in separate databases based on the separate categories; and generating a report based on the parsed unstructured demographic data that displays the parsed unstructured demographic data in a structured format.

11. The program storage device of claim 10, wherein the navigating comprises iteratively accessing the respective site for a predetermined number of attempts when the corresponding data source or the respective site is initially inaccessible.

12. The program storage device of claim 11, the instructions further comprising receiving an error notification when the corresponding data source or the respective site is inaccessible after completing the predetermined number of attempts.

13. The program storage device of claim 10, wherein the user interface further indicates a color code indicator of a priority level of each of the plurality of data sources.

14. The program storage device of claim 10, the instructions further comprising managing a plurality of data extractors performing tasks on each of the plurality of data sources.

15. The program storage device of claim 14, wherein managing the plurality of data extractors comprises managing a maximum number of data extractors performing tasks on each of the plurality of data sources.

16. The program storage device of claim 15, wherein when the maximum number of data extractors for a first data source of the plurality of data sources is reached, the method further comprises assigning tasks of a second data source of the plurality of data sources having a same priority level as the first data source.

17. The program storage device of claim 15, wherein when the maximum number of data extractors for a first data source is reached, the method further comprises assigning tasks of a second data source of the plurality of data sources having a different priority level as the first data source.

18. The program storage device of claim 14, wherein managing the plurality of data extractors comprises periodically adjusting the plurality of data extractors performing tasks on the corresponding data source.

19. A system comprising:
a first computing device comprising:
a first memory; and
a first processor communicatively coupled to the first memory and configured to:
generate a decision tree for a data source of a plurality of data sources, wherein the decision tree comprises a base website at a root node and a plurality of respective sites represented as corresponding leaf nodes of the decision tree, wherein the decision tree specifies one or more paths to navigate from the base website to the plurality of respective sites containing unstructured demographic data for a healthcare provider, wherein each of the plurality of respective sites and the corresponding leaf nodes of the decision tree represent a step in the decision tree, wherein a respective site is a website accessible from the base website of the data source;
generate a list of tasks for each of the plurality of data sources based on the decision tree, wherein each task includes instructions for how to extract the unstructured demographic data corresponding to the respective site of the one or more paths and comprises instructions for extracting the unstructured demographic data from the respective site;
assign a task from the list of tasks to a second computing device based on a priority level of a corresponding data source;
generate a user interface to be presented on a display, wherein the user interface indicates the list of tasks to be performed for each of the plurality of data sources and a status for the list of tasks; and
transmit the assigned task to the second computing device; the second computing device comprising:
a second memory; and
a second processor communicatively coupled to the second memory and configured to:
execute the assigned task to navigate, based on the decision tree, the corresponding data source to the respective site and extract the unstructured demographic data from the respective site based on the assigned task; and
transmit the extracted unstructured demographic data to the first computing device, wherein upon receipt of the extracted unstructured demographic data, the first processor is further configured to:
parse the extracted unstructured demographic data into separate categories;
store the parsed unstructured demographic data in separate databases based on the separate categories; and
generate a report based on the parsed unstructured demographic data that displays the parsed unstructured demographic data in a structured format.

20. The system of claim 19, wherein the user interface further indicates a color code indicator of a priority level of each of the plurality of data sources.

* * * * *